(12) United States Patent
Weiner et al.

(10) Patent No.: US 6,733,994 B2
(45) Date of Patent: May 11, 2004

(54) HIGHLY EXPRESSIBLE GENES

(75) Inventors: David B. Weiner, Merion Station, PA (US); Joo-Sung Yang, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 26 days.

(21) Appl. No.: 09/971,806

(22) Filed: Oct. 4, 2001

(65) Prior Publication Data

US 2002/0123099 A1 Sep. 5, 2002

Related U.S. Application Data

(60) Provisional application No. 60/237,885, filed on Oct. 4, 2000.

(51) Int. Cl.[7] .............................................. C12P 21/02
(52) U.S. Cl. ........................................ 435/69.1; 536/23.1
(58) Field of Search .......................... 435/69.1, 320.1; 514/44; 536/23.1; 702/20, 19

(56) References Cited

U.S. PATENT DOCUMENTS

| | | | |
|---|---|---|---|
| 4,722,848 A | 2/1988 | Paoletti et al. | 424/199.1 |
| 4,945,050 A | 7/1990 | Sanford et al. | 435/459 |
| 5,017,487 A | 5/1991 | Stunnenberg et al. | 435/91.41 |
| 5,036,006 A | 7/1991 | Sanford et al. | 435/459 |
| 5,077,044 A | 12/1991 | Stocker | 424/235.1 |
| 5,110,587 A | 5/1992 | Paoletti et al. | 424/199.1 |
| 5,112,749 A | 5/1992 | Brey, III et al. | 435/172.3 |
| 5,174,993 A | 12/1992 | Paoletti | 424/199.1 |
| 5,223,424 A | 6/1993 | Cochran et al. | 435/236 |
| 5,225,336 A | 7/1993 | Paoletti | 435/69.1 |
| 5,240,703 A | 8/1993 | Cochran | 424/205.1 |
| 5,242,829 A | 9/1993 | Panicali et al. | 435/320.1 |
| 5,254,463 A | 10/1993 | de Boer et al. | 435/69.4 |
| 5,294,441 A | 3/1994 | Curtiss, III | 424/200.1 |
| 5,294,548 A | 3/1994 | McLinden et al. | 435/235.1 |
| 5,310,668 A | 5/1994 | Ellis et al. | 435/320.1 |
| 5,387,744 A | 2/1995 | Curtiss, III et al. | 424/258.1 |
| 5,389,368 A | 2/1995 | Gurtiss, III | 424/200.1 |
| 5,424,065 A | 6/1995 | Curtiss, III et al. | 424/93.2 |
| 5,451,499 A | 9/1995 | Cochran | 435/5 |
| 5,453,364 A | 9/1995 | Paoletti | 435/69.3 |
| 5,462,734 A | 10/1995 | Letchworth, III et al. | 424/229.1 |
| 5,470,734 A | 11/1995 | Sondermeijer et al. | 424/229.1 |
| 5,482,713 A | 1/1996 | Paoletti | 424/199.1 |
| 5,489,529 A | 2/1996 | de Boer et al. | 435/243 |
| 5,580,859 A | 12/1996 | Felgner et al. | 514/44 |
| 5,593,972 A | 1/1997 | Weiner et al. | 514/44 |
| 5,676,594 A | 10/1997 | Joosten | 452/188 |
| 5,703,055 A | 12/1997 | Felgner et al. | 514/44 |
| 5,739,118 A | 4/1998 | Carrano et al. | 514/44 |
| 5,817,637 A | 10/1998 | Weiner et al. | 514/44 |
| 5,830,876 A | 11/1998 | Weiner et al. | 514/44 |
| 5,962,428 A | 10/1999 | Carrano et al. | 514/44 |
| 5,965,726 A | 10/1999 | Pavlakis et al. | 536/23.72 |
| 5,972,596 A | 10/1999 | Pavlakis et al. | 435/5 |
| 5,981,505 A | 11/1999 | Weiner et al. | 514/44 |

OTHER PUBLICATIONS

Chaudhary, V. et al., "A rapid method of cloning functional variable–region antibody genes in *Escherichia coli* as single–chain immunotoxins," *Proc Natl Acad Sci USA*, 1990, 87, 1066.

Freier, S. et al., "Improved free–energy parameters for predictions of RNA duplex stability," *Proc Natl Acad Sci USA*, 1986, 83, 9373–9377.

Jaeger, J. et al., "Improved predictions of secondary structures for RNA," *Proc Natl Acad Sci USA*, 1989, 86, 7706–7710.

Howell, M. et al., "Limited T–cell receptor β–chain heterogeneity among interleukin 2 receptor–positive synovial T cells suggests a role for superantigen in rheumatoid arthritis," *Proc Natl Acad Sci USA*, 1991, 88, 10921–10925.

Kim, C. et al., "Codon optimization for high–level expression of human erythropoietin (EPO) in mammalian cells," *Gene* 1991, 199, 293–301.

Oksenberg, J. et al., "Limited heterogeneity of rearranged T–cell receptor V α transcripts in brains of multiple sclerosis patients," *Nature*, 1990 345, 344–346.

Paliard, X. et al., "Evidence for the Effects of a Superantigen in Rheumatoid Arthritis," *Science*, 1991, 253, 325–329.

Williams, W. et al., "Restricted Heterogeneity of T Cell Receptor Transcripts in Rheumatoid Synovium," *J Clin Invest*, 1992, 90, 326–333.

Wucherpfennig, K. et al., "Shared Human T Cell Receptor $V_\beta$Usage to Immunodominant Regions of Myelin Basic Protein," *Science*, 1990, 248, 1016–1019.

(List continued on next page.)

*Primary Examiner*—James Martinell
(74) *Attorney, Agent, or Firm*—Cozen O'Connor, P.C.

(57) ABSTRACT

The present invention provides methods of producing protein in a recombinant expression system that comprises translation of mRNA transcribed from a heterologous DNA sequence in the expression system, said method comprising the steps of predicting the secondary structure of mRNA transcribed from a native heterologous DNA sequence; modifying the native heterologous DNA sequence to produce a modified heterologous DNA sequence wherein mRNA transcribed from the modified heterologous DNA sequence has a secondary structure having increased free energy compared to that of the secondary structure of the mRNA transcribed from the native heterologous DNA sequence; and using the modified heterologous DNA sequence in the recombinant expression system for protein production. The invention also provides injectable pharmaceutical compositions comprising a nucleic acid molecule that includes a modified coding sequence. The invention also provides recombinant viral vectors comprising a nucleic acid molecule that includes a modified coding sequence.

10 Claims, 11 Drawing Sheets

OTHER PUBLICATIONS

Zuker, M., "On finding all suboptimal foldings of an RNA molecule," *Science*, 1989, 244, 48–52.

de Smit, M.H., et al "Control of translation by mRNA secondary structure in *Escherichia coli*," *J. Mol. Biol.*, 1994, 244, 144–150.

Mukund, M.A., et al., "Effect of mRNA secondary structure in the regulation of gene expression: unfolding of stable loop causes the expression of Taq polymerase in *E. coli*," *Current Science*, Jun. 10, 1999, 76(11), 1486–1490.

Suo, Z., et al., "RNA secondary structure switching during DNA synthesis catalyzed by HIV–1 reverse transcriptase," *Biochemistry*, 1997, 36, 14778–14785.

Fig.1.

```
                                              Kozak sequence
                   HindIII linker
                                    20                      40                      60
1.sIgEh-WNVChu   CCC AAG CTT GCC GCC ACC ATG GAC TGG ACC TGG ATC CTG TTC CTG GTG GCC GCC GCC ACC
2.sIgEy-WNVCy*   ... ... ... ... ... ... ..t ... ..t ... ... t.a ..t t.a ..t ..t ..t ..t ..t M   D   W   T   W   I   L   F   L   V   A   A   A   T
4.sIgEori                                ATG GAC TGG ACC TGG ATC CTc TTC tTG GTG GCa GCa GCC ACg ┌─ WNVC orf
                                    80                      100                     120
                 S   K   K   P   G   G   P   G   K   S   R   A   V   N   M   L
1.sIgEh-WNVChu   CGC GTG CAC ACC TCT AAG AAA CCA GGA GGC CCC GGC AAG AGC CGC GCC GTG AAC ATG CTG
2.sIgEy-WNVCy*   a.a ..t ..t tct ... ..a ... ... ..t ... ... ... ... ... ... ... ... ... ...
3.WNVCwt         ... ... ... ... ... ... ... ..g ... ... ... ... ..g ..t ..c ..t ... ..a R   V   H   S
4.sIgEori    CGa GTc CAC tcC
                 ←─┘
             sIgE leader sequence
                                    140                     160                     180
                 K   R   G   M   P   R   V   L   S   L   I   G   L   K   R   A   M   L   S   L
1.sIgEh-WNVChu   AAG CGC GGC ATG CCC CGC GTG CTG AGC CTG ATT GGC CTG AAG CGC GCC ATG CTG AGC CTG
2.sIgEy-WNVCy*   ... ... ... ... ... ... ... ... ... ... ... ... ... ... ... ... ... ... ... ...
3.WNVCwt         ..a ... ..a ... ... ... ... ... t.. tc. t.. ... ..a ... a.g ..t ... t.. ... ...

200                     220                     240
                 I   D   G   K   G   P   I   R   F   V   L   A   L   L   A   F   F   R   F   T
1.sIgEh-WNVChu   ATC GAC GGC AAG GGC CCC ATA CGC TTC GTG CTG GCC CTG CTG GCC TTC TTC CGC TTC ACC
2.sIgEy-WNVCy*   ... ... ... ... ... ... ... ... ... ... ... ... ... ... ... ... ... ... ... ...
3.WNVCwt         ... ... ... ... ..g ..a ... ..a ..t ... t.. ..t ..c t.. ..g ... ... a.g ... ..a 260                     280                     300
                 A   I   A   P   T   R   A   V   L   D   R   W   R   G   V   N   K   Q   T   A
1.sIgEh-WNVChu   GCC ATT GCC CCC ACC CGC GCC GTG CTG GAC CGC TGG CGC GGC GTG AAC AAG CAG ACC GCC
2.sIgEy-WNVCy*   ... ... ... ... ... ... ... ... ... ... ... ... ... ... ... ... ... ... ... ...
3.WNVCwt         ..a ... ..t ..g ... ..a ..a ... ... ..t ..a ... a.a ..t ... ... ..a ..a ..a ..g 320                     340                     360
                 M   K   H   L   L   S   F   K   K   E   L   G   T   L   T   S   A   I   N   R
1.sIgEh-WNVChu   ATG AAG CAC CTG CTG AGC TTC AAG AAG GAG CTG GGC ACC CTG ACC AGC GCC ATC AAC CGC
2.sIgEy-WNVCy*   ... ... ... ... ... ... ... ... ... ... ... ... ... ... ... ... ... ... ... ...
3.WNVCwt         ... ..a ... ..t ... ..t ..t ... ... ..a ..a ..g ... t.. ... ..t ..t ... ..t ..g 380                     400                     420
                 R   S   S   K   Q   K   K   R   G   G   K   T   G   I   A   V   M   I   G   L
1.sIgEh-WNVChu   CGC AGC AGC AAG CAG AAG AAG CGC GGC GGC AAG ACC GGC ATT GCC GTG ATG ATT GGC CTG
2.sIgEy-WNVCy*   ... ... ... ... ... ... ... ... ... ... ... ... ... ... ... ... ... ... ... ...
3.WNVCwt         ..g ... tca ..a ..a ... ..a a.a ..a ..a ... ... ..a ... ... ..a ..c ... ... ...

NotI linker
                 I   A   S   V   G   A
1.sIgEh-WNVChu   ATC GCC AGC GTG GGC GCG GCC GCT AAA CTA T
2.sIgEy-WNVCy*   ... ... ... ... ... ... ... ... ... ... .
3.WNVCwt         ... ... ... ..a ..a ..a
``` mRNA Energy Minimization in 1st 73 Bases

WNVwt     WNVh-DJY     WNVy-DJY

FIG. 2

ENERGY = -15.1
*wild type

ENERGY = -18.6
*human codon

ENERGY = -8.3
*yeast codon

Fig. 3 Immunoprecipitation of Radiolabeled *In Vitro* Translated Proteins mRNA Energy Minimization: Addition of Leader Sequence mRNA Energy Minimization with 1st 200 bases

FIG. 11
WNV Env RNA Optimization

204 ENERGY = -54.2
WNVwt200 Length: 200    Oc

204 ENERGY = -58.9
WNVhu200 Length: 200    Oc

205 ENERGY = -47.4
WNVyt200 Length: 201    Oc

HIGHLY EXPRESSIBLE GENES

CROSS-REFERENCE TO RELATED APPLICATIONS

This application claims priority to U.S. Provisional Patent Application Ser. No. 60/237,885, filed Oct. 4, 2000, which is incorporated herein by reference.

FIELD OF THE INVENTION

The present invention relates generally to the fields of gene expression, gene therapy, and genetic immunization.

BACKGROUND OF THE INVENTION

The expression of a protein gene product is influenced by many factors, including gene copy number, gene integration site or gene location in the genome, transcription factors, mRNA stability, and translation efficiency. For example, the expression of the human immunodeficiency virus-1 (HIV-1) structural genes gag, pol, and env is dependent on the Rev/Rev-responsive element (RRE) at a posttranscriptional level. This dependency on Rev is a limiting factor for gene expression. In addition, highly stable RNA secondary structures that form in various regions of the HIV RNA transcript can block or otherwise interfere with ribosome movement, and thus effectively limit translation. Formation of stable RNA secondary structures in gene transcripts is a general phenomenon that can limit the translational yield of many protein gene products for a wide variety of genes.

Kim et al., 1997, Gene, 199:293–301, which is incorporated herein by reference, optimized expression of human erythropoietin (EPO) in mammalian cells by altering the codons encoding the leader sequence and the first 6 amino acids of the mature EPO protein for the most prevalently used yeast codons, and changing the codons encoding the rest of the EPO protein for the most prevalently used human codons.

U.S. Pat. Nos. 5,972, 596 and 5,965,726 (Pavlakis et al.), which are incorporated herein by reference, describe methods of locating an inhibitory/instability sequence or sequences (INS: sequences that render an mRNA unstable or poorly utilized/translated) within the coding region of an mRNA and modifying the gene encoding the mRNA to remove the inhibitory/instability sequences with clustered nucleotide substitutions.

There is a need for new methods of expressing proteins and methods of increasing the level of protein expression of therapeutic and immunogenic transgenes. There is a need for methods of increasing the translational yields of any protein gene product. There is a need for methods of overcoming the limitations imposed by RNA secondary structure in RNA transcripts upon the ultimate level of protein expression of any gene. The present invention is directed to addressing these and other needs.

SUMMARY OF THE INVENTION

The present invention provides methods of producing protein in a recombinant expression system that comprises translation of mRNA transcribed from a heterologous DNA sequence in the expression system, said method comprising the steps of predicting the secondary structure of mRNA transcribed from a native heterologous DNA sequence; modifying the native heterologous DNA sequence to produce a modified heterologous DNA sequence wherein mRNA transcribed from the modified heterologous DNA sequence has a secondary structure having increased free energy compared to that of the secondary structure of the mRNA transcribed from the native heterologous DNA sequence; and using the modified heterologous DNA sequence in the recombinant expression system for protein production. The recombinant expression system may be a cell free in vitro transcription and translation system, an in vitro cell expression system, a DNA construct used in direct DNA injection, or a recombinant vector for delivery of DNA to an individual. The secondary structure of the mRNA transcribed from a native heterologous DNA sequence may be predicted using a computer and computer program. The native heterologous DNA sequence may be modified by increasing the AT content of the coding sequence, in particular, at the 5' end of the coding sequence, or at the 5' end of the coding sequence within 200, 150, or 100 nucleotides from the initiation codon.

The present invention also provides injectable pharmaceutical compositions comprising a nucleic acid molecule that includes a modified coding sequence encoding a protein operably linked to regulatory elements, wherein the modified coding sequence comprises a higher AT or AU content relative to the AT or AU content of the native coding sequence, and further comprising a pharmaceutically acceptable carrier. The encoded proteins may be immunogens or non-immunogenic therapeutic proteins. The modifications may be within the first 100 to 200 bases of the coding sequence, within stretches of sequences dispersed throughout the coding sequence, or within in the last 100 to 200 bases.

The present invention also provides recombinant viral vectors comprising a nucleic acid molecule that includes a modified coding sequence encoding a protein operably linked to regulatory elements, wherein the modified coding sequence comprises a higher AT or AU content relative to the AT or AU content of the native coding sequence.

BRIEF DESCRIPTION OF THE DRAWINGS

FIG. 1 presents the nucleotide and amino acid sequence of the West Nile Virus (WNV) wild type capsid (Cp) protein (WNVC) with constructs (WNVChu and WNVCy*) modified on the basis of RNA secondary structure. A secretory IgE signal leader sequence was fused to the WNVC protein. To avoid varied expression levels due to the linear sequence between the promoter and 5'-proximal region of the WNVC, the leader sequences and the codons for amino acids 2–6 of the WNVC were modified with yeast (WNVCy) or human (WNVChu) optimized codons. However, the remaining portion of the coding sequence for the WNV capsid protein, in both constructs, was modified with human optimized codons. Presented are 1) the wild type nucleotide sequence encoding the sIgE leader sequence (4. sIgEori) (SEQ ID NO: 1), 2) the amino acid sequence of the sIgE leader sequence (appearing above the nucleotide sequence) (SEQ ID NO:2), 3) the amino acid sequence for the WNV capsid protein (minus the initial methionine) (SEQ ID NO:3), and 4) the nucleotide sequence of the sIgEh-WNV capsid protein encoding sequence of the WNVChu construct (1. sIgEh-WNVChu) (SEQ ID NO:4). Differences in the coding sequence for sIgEh-WNV capsid protein in the WNVCy construct (2. sIgEy-WNVCy*) and in the wild type WNV capsid encoding sequence (3. WNVCwt) are indicated below the nucleotide sequence of the WNVChu construct.

FIG. 2 presents the MulFold predicted RNA secondary structures with free energy values for the first 73 nucleotides of 1) the wild type mRNA encoding WVN capsid protein (WNVwt), 2) an mRNA encoding the sIgE leader/WNV capsid protein containing human optimized codons (WNVh-DJY), and 3) an mRNA encoding the sIgE leader/WNV capsid protein containing yeast optimized codons (WNVy-DJY). The last codon (GGC for glycine) shown for the WNVy-DJY sequence is human optimized. As shown, "T" represents "U" in the RNA strands. The nucleotides of the mRNA strands that encode the sIgE leader portion of the fusions in WNVh-DJY and WNVy-DJY are shown in bold.

FIG. 11 presents the MulFold predicted secondary structures and overall free energy values for the first 200 nucleotides of the mRNA transcript for 1) the wild type West Nile Virus (WNV) envelope (env) gene (WNVwt200), 2) the WNV env gene optimized with the most prevalently used codons in humans (WNVhu200), and 3) the WNV env gene having codons that are utilized less prevalently in humans (yeast optimized, WNVyt200). As shown, "T" represents "U" in the RNA strands.

DESCRIPTION OF THE PREFERRED EMBODIMENTS

Figure 3:
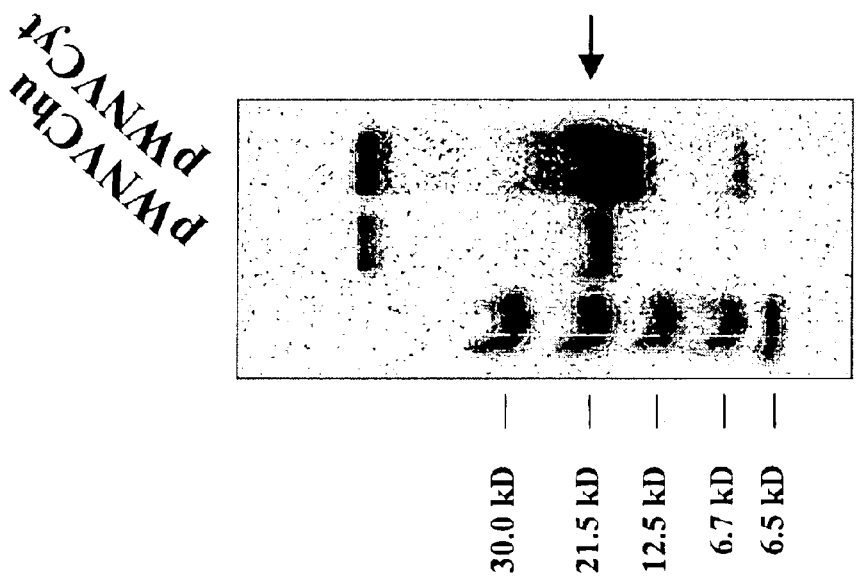
FIG. 3 presents an autoradiograph of electrophoretically separated, immunoprecipitated, radiolabeled in vitro transcription/translation products from two different WNV capsid protein constructs: pWNVChu (also called WNVChu and pWNVh-DJY) and pWNVCyt (also called WNVCy and pWNVy-DJY). The first lane on the left contains molecular weight markers. The arrow indicates the position of the main capsid protein product. The proteins, which are fusions with polyhistidine C-terminal tags, were immunoprecipitated using an anti-His antibody.

The present invention is based upon the discovery that enhancement of protein expression can be achieved by increasing the free energy of and destabilizing RNA secondary structure through changes at the nucleotide level. It has been discovered that an increase in the free energy (×kcal) of an RNA transcript will result in increased expression of the protein that it encodes. In preferred embodiments, an increase in the free energy (×kcal) within a 200 base segment of an RNA transcript will result in increased expression of the protein that it encodes. The segment is preferably at the 5' end, usually including the initiation codon. In some embodiments, the segment is preferably 200 bases, 150 bases, or 100 bases. The secondary structure of an RNA molecule is the collection of base pairs that occur in its three-dimensional structure. The secondary structure of a given RNA molecule can be predicted and such predicted secondary structure will have an assigned overall free energy value. It has been discovered that alterations to the primary sequence of an RNA transcript that result in an increase to the minimum predicted overall free energy for a predicted secondary structure for that RNA, or that increase the minimum predicted free energy for a predicted secondary structure for regions of that RNA, will promote increased expression of the protein encoded by that RNA transcript. This strategy for the optimization of protein expression applies to any situation where expression is desired, including, but not limited to: in vivo, including, but not limited to, DNA vaccines, live vaccines, gene therapeutics, and transgenes; in vitro, including, but not limited to, recombinant manufacturing procedures using such systems as prokaryotic and eukaryotic (mammal, insect, and yeast) cells in culture; ex vivo, including, but not limited to, systems where cells receive expression constructs and are implanted into recipient organisms; and any other expression system where it is desirable to express a gene of interest or increase the expression of a gene.

One aspect of the invention is to generate an RNA encoding a protein that promotes efficient expression of that protein or that leads to increased levels of expression of the protein. Alterations to the sequence of the DNA encoding the RNA that lead to an increase in the minimum overall free energy for the predicted secondary structure of that RNA, or that increase the minimum free energy for the predicted secondary structure of one or more regions of that RNA promote efficient and/or increased expression of the encoded protein.

Increases to the free energy of the secondary structure of an RNA can be monitored by analyzing various altered versions of a sequence with a program like MFOLD, which calculates and predicts the most stable structure for an input sequence based upon energy minimization. MFOLD is computer software designed by Zuker, Jaeger, and colleagues (see Zuker, 1989, On finding all suboptimal foldings of an RNA molecule, Science, 244:48–52, and Jaeger et al., 1989, Improved predictions of secondary structures for RNA, Proc. Natl. Acad. Sci. USA, 86:7706–7710, each of which is incorporated herein by reference) that is used for the prediction of RNA secondary structure by free energy minimization, using energy rules developed by Turner and colleagues (see Freier et al., 1986, Proc. Natl. Acad. Sci. USA, 83:9373–9377, which is incorporated herein by reference). MulFold is the Macintosh version of MFOLD. LoopDloop is a secondary structure drawing program. The most stable structure will be the one with a minimum overall free energy. The more negative the value of the free energy for the structure, the more stable. Alterations to the sequence of the RNA that are predicted to result in a secondary structure having an overall higher free energy value, are destabilizing alterations which result in less stable RNA secondary structure and which promote efficient translation of the RNA and an increase in protein expression.

The practice of the present invention will employ, unless otherwise indicated, conventional methods of virology, immunology, microbiology, molecular biology, and recombinant DNA techniques within the skill of the art. Such techniques are explained fully in the literature. See, e.g., Sambrook et al., eds., Molecular Cloning: A Laboratory Manual ($3^{rd}$ ed.) Cold Spring Harbor Laboratory Press, Cold Spring Harbor, N.Y. (2001); Ausubel et al., eds., Current Protocols in Molecular Biology, John Wiley & Sons, New York, N.Y. (2001); Glover & Hames, eds., DNA Cloning 3: A Practical Approach, Vols. I, II, & III, IRL Press, Oxford (1995); Colowick & Kaplan, eds., Methods in Enzymology, Academic Press; Weir et al., eds., Handbook of Experimental Immunology, $5^{th}$ ed., Blackwell Scientific Publications, Ltd., Edinburgh, (1997); Fields, Knipe, & Howley, eds., Fields Virology ($3^{rd}$ ed.) Vols. I & II, Lippincott Williams & Wilkins Pubs. (1996); Flint, et al., eds., Principles of Virology: Molecular Biology, Pathogenesis, and Control, ASM Press, (1999); Coligan et al., eds., Current Protocols in Immunology, John Wiley & Sons, New York, N.Y. (2001), each of which is incorporated herein by reference.

Various definitions are made throughout this document. Most words have the meaning that would be attributed to those words by one skilled in the art. Words specifically defined either below or elsewhere in this document have the meaning provided in the context of the present invention as a whole and as typically understood by those skilled in the art.

As used herein, the term "recombinant expression system" refers to any nucleic acid based approach or system for the expression of a gene product or gene products of interest, that has been artificially organized (man made) of components directed toward the expression of the gene product or products. The components may be of naturally occurring genetic sources, synthetic or artificial, or some combination of natural and artificial genetic elements. Generally the gene product is a protein, polypeptide, or peptide. Examples of recombinant expression systems include, but are not limited to, a cell free in vitro transcription and translation system; an in vitro cell expression system; a DNA construct used in direct DNA injection; and a recombinant vector for delivery of DNA to an individual.

As used herein, the term "heterologous DNA sequences" refers to deoxyribonucleic acid based sequences that are in a non-natural context, for example, in a recombinant construct, plasmid, or virus, or inserted into a non-natural position in a chromosome, or introduced into a non-natural or foreign cell. "Heterologous DNA sequence" refers to any DNA sequence that is foreign or not naturally associated with the other DNA sequences to which it is associated or linked (operably or otherwise), or a DNA sequence that is not naturally associated with the cell or organism into which it is introduced. An example of a heterologous DNA sequence is one that is used for the expression of a foreign or heterologous protein gene product in a host cell or organism. A heterologous DNA sequence can also be a part of a vector or expression construct having genetic material designed for directing the expression of a gene product, such as a protein, polypeptide, or peptide, in a host cell in vivo or in vitro, or in a cell free in vitro expression system.

As used herein, the term "native heterologous DNA sequence" refers to a heterologous DNA sequence that, although positioned in a non-natural context, has a nucleotide sequence that is not modified or altered from the sequence it has in its natural context. For example, a viral gene may be inserted into a recombinant expression construct, such that the viral gene is a heterologous DNA sequence with respect to other sequences in the construct, but without introduction of any changes to the nucleotide sequence of the viral gene. In this example, as a native heterologous DNA sequence, the viral gene has the native nucleotide sequence as would be found in its natural context within the genome of the virus, but the viral gene sequence is heterologous with respect to its new context. A native heterologous DNA sequence can also be any DNA sequence that is considered to be the reference or starting version of a DNA sequence, from which a modified (non-native) version of the DNA sequence, containing alterations to the nucleic acid sequence may be prepared. A native heterologous DNA sequence can also be composed of multiple native DNA sequences that are unaltered in sequence from that which is found in nature, but that are not naturally found together. An example of such a native heterologous DNA sequence composed of multiple native DNA sequences is a fusion gene composed of native genetic sequence from two different genes.

As used herein, the term "modified heterologous DNA sequence" refers to a heterologous DNA sequence that is not only positioned in a non-natural context, but also has a nucleotide sequence that is modified or altered from the sequence it has in its natural context. For example, a viral gene that is a modified heterologous DNA sequence will be inserted into a recombinant expression construct, such that the viral gene is heterologous with respect to other sequences in the construct, and further, will have a nucleotide sequence that is modified or altered and not the native nucleotide sequence as found in its natural context within the genome of the virus.

As used herein, the term "increased free energy" in reference to RNA secondary structure, refers to an increase in the free energy value for an RNA secondary structure. Free energy values that are more negative are lower than values that are less negative.

As used herein, the term "modified coding sequence" refers to a nucleic acid sequence (DNA- or RNA-based), that encodes a gene product, protein, polypeptide, or peptide, and that has been modified or altered from the native or naturally-occurring coding sequence for that gene product, protein, polypeptide, or peptide. The coding sequence may be comprised of sequences from more than one genetic source, for example, the coding sequence may be a fusion gene encoding a fusion protein having a leader sequence from a gene for one protein and the remaining sequence from a gene for another protein, brought together as one hybrid coding sequence, that is non-natural. In the case of such an example of a coding sequence comprised of sequences from more than one genetic source, "modified coding sequence" indicates that any modification is relative to the native or naturally-occurring coding sequence for the respective separate sequences.

As used herein, the term "native coding sequence" refers to a nucleic acid sequence (DNA- or RNA-based), that encodes a gene product, protein, polypeptide, or peptide, and that has not been modified or altered from the native or naturally-occurring coding sequence for that gene product, protein, polypeptide, or peptide. If the coding sequence encodes a fusion protein, the component parts have not been modified or altered from the native or naturally-occurring coding sequence for those component parts.

As used herein, the term "higher AT or AU content" refers to modifications to a coding sequence which render it a "modified coding sequence" such that if it is DNA-based it has a higher concentration of adenine and thymidine residues than the corresponding native coding sequence, and if it is RNA-based it has a higher concentration of adenine and uridine residues than the corresponding native coding sequence.

As used herein, the term "the first 200 bases" in reference to a modified coding sequence that has been modified relative to the native coding sequence, refers to the first 200 contiguous nucleotide bases from the 5' end of the respective coding sequence.

As used herein, the term "the first 150 bases" in reference to a modified coding sequence that has been modified relative to the native coding sequence, refers to the first 150 contiguous nucleotide bases from the 5' end of the respective coding sequence.

As used herein, the term "the first 100 bases" in reference to a modified coding sequence that has been modified relative to the native coding sequence, refers to the first 100 contiguous nucleotide bases from the 5' end of the respective coding sequence.

As used herein, the term "the last 200 bases" in reference to a modified coding sequence that has been modified relative to the native coding sequence, refers to the last 200 contiguous nucleotide bases from the 3' end of the respective coding sequence.

As used herein, the term "the last 150 bases" in reference to a modified coding sequence that has been modified relative to the native coding sequence, refers to the last 150 contiguous nucleotide bases from the 3' end of the respective coding sequence.

As used herein, the term "the last 100 bases" in reference to a modified coding sequence that has been modified relative to the native coding sequence, refers to the last 100 contiguous nucleotide bases from the 3' end of the respective coding sequence.

As used herein, the term "region of up to 200 bases in length" in reference to a coding sequence, refers to a region of up to 200 contiguous nucleotide bases of the coding sequence. The region may be anywhere within the coding sequence.

As used herein, the term "region of up to 150 bases in length" in reference to a coding sequence, refers to a region of up to 150 contiguous nucleotide bases of the coding sequence. The region may be anywhere within the coding sequence.

As used herein, the term "region of up to 100 bases in length" in reference to a coding sequence, refers to a region of up to 100 contiguous nucleotide bases of the coding sequence. The region may be anywhere within the coding sequence.

As used herein, the term "dispersed modifications" refers to any combination of at least two regions of contiguous nucleotide bases that are modified to have a higher AT or AU content relative to the native coding sequence in the respective regions, and that are dispersed throughout the sequence such that regions of modified coding sequences will alternate with regions of native coding sequence. By way of non-limiting example, a modified coding sequence may contain alternating regions of modifications, wherein the first 200 contiguous bases of the coding sequence have a higher AT or AU content relative to the native coding sequence, the next 200 bases of the coding sequence are non-modified relative to the native coding sequence, and the subsequent 200 contiguous base region is modified to have a higher AT or AU content relative to the native coding sequence. The size of the modified regions may be of any length, and is preferably 200, 150, or 100 bases in length. The size of non-modified regions will be of variable length depending on the positioning of the modified regions. In preferred embodiments the dispersed modifications comprise alternating regions of modified and native coding sequence over the entire coding sequence, where the size of each alternating region is preferably 200 or 150 or 100 bases in length.

As used herein, "injectable pharmaceutical composition" refers to pharmaceutically acceptable compositions for use in patients that are sterile, pyrogen-free, and essentially free of any particulates or particulate matter. See, *Remington's Pharmaceutical Sciences*, 18$^{th}$ Ed., Gennaro, ed., Mack Publishing Co., Easton, Pa., 1990 and U.S.P., the standards of the U.S. Pharmacopeia, which is incorporated herein by reference.

As used herein, "pharmaceutically acceptable carrier" includes any carrier that does not itself induce a harmful effect to the individual receiving the composition. For example, a "pharmaceutically acceptable carrier" should not induce the production of antibodies harmful to the recipient. Suitable "pharmaceutically acceptable carriers" are known to those of skill in the art and are described in *Remington's Pharmaceutical Sciences*, supra.

As used herein the term "target protein" is meant to refer to peptides and proteins encoded by gene constructs of the present invention which act as target proteins for an immune response. The terms "target protein" and "immunogen" are used interchangeably and refer to a protein against which an immune response can be elicited. The target protein is an immunogenic protein which shares at least an epitope with a protein from the pathogen or undesirable cell-type such as a cancer cell or a cell involved in autoimmune disease against which an immune response is desired. The immune response directed against the target protein will protect the individual against and/or treat the individual for the specific infection or disease with which the target protein is associated.

As used herein the term "desired protein" is meant to refer to peptides and proteins encoded by gene constructs of the present invention which either act as target proteins for an immune response or as a therapeutic or compensating protein in gene therapy regimens.

As used herein, the phrase "immunogenic fragment thereof" in reference to an immunogen, refers to fragments of less than the full length of the immunogen against which an immune response can be induced.

As used herein, the term "cancer antigens" refers to any proteins, polypeptides, or peptides, and the like, that are associated with and/or serve as markers for cancer, tumors, or cancer cells.

As used herein, the term "autoimmune disease associated proteins" refers to any proteins, polypeptides, or peptides, and the like, that are associated with and/or serve as markers for cells involved in and/or responsible for an autoimmune disease.

As used herein, the term "non-immunogenic therapeutic protein" refers to such proteins, polypeptides, and peptides that are useful for therapeutic treatment of various diseases and disorders, and to which an immune response is not desired and/or not expected upon their introduction into the body of a recipient organism, patient, or individual in need of such therapy or treatment. Examples of "non-immunogenic therapeutic proteins" are proteins that are missing or in low concentration in an individual having a genetic defect in the endogenous gene encoding the protein. Examples of "non-immunogenic therapeutic proteins" include, but are not limited to, cytokines, growth factors, blood products, and enzymes.

As used herein, the term "recombinant viral vector" refers to a construct, based upon the genome of a virus, that can be used as a vehicle for the delivery of nucleic acids encoding proteins, polypeptides, or peptides of interest. Recombinant viral vectors are well known in the art and are widely reported. Recombinant viral vectors include, but are not limited to, retroviral vectors, adenovirus vectors, and adeno-associated virus vectors, which are prepared using routine methods and starting materials.

As used herein, the term "genetic construct" refers to the DNA or RNA molecules that comprise a nucleotide sequence which encodes a target protein or immunomodulating protein. The coding sequence includes initiation and termination signals operably linked to regulatory elements including a promoter and polyadenylation signal capable of directing expression in the cells of the individual to whom the nucleic acid molecule is administered.

As used herein, the term "expressible form" refers to gene constructs which contain the necessary regulatory elements operably linked to a coding sequence that encodes a target protein or an immunomodulating protein, such that when present in the cell of the individual, the coding sequence will be expressed.

As used herein, the term "sharing an epitope" refers to proteins which comprise at least one epitope that is identical to or substantially similar to an epitope of another protein.

As used herein, the term "substantially similar epitope" is meant to refer to an epitope that has a structure which is not identical to an epitope of a protein but nonetheless invokes a cellular or humoral immune response which cross reacts to that protein.

As used herein, the term "intracellular pathogen" is meant to refer to a virus or pathogenic organism that, during at least part of its reproductive or life cycle, exists within a host cell and therein produces or causes to be produced, pathogen proteins.

As used herein, the term "hyperproliferative diseases" is meant to refer to those diseases and disorders characterized by hyperproliferation of cells.

As used herein, the term "hyperproliferative-associated protein" is meant to refer to proteins that are associated with a hyperproliferative disease and/or hyperproliferative cells.

In some preferred embodiments, it is preferred that the alterations to the RNA do not alter the sequence of the protein. In some preferred embodiments, it is preferred that the 200 bases, within which the alterations are introduced, are at the 5' end of the RNA transcript. In some embodiments, it is preferred to increase the free energy in more than one segment of the RNA transcript. Optionally, a leader sequence may be added to increase the free energy of the secondary structure of the RNA.

A stable RNA secondary structure at the 5' end of open reading frame (orf) sequences may block efficient transcription by interfering with ribosome function. Many RNAs have highly stable secondary structural integrity, and these interactions can inhibit gene expression Addition of a sequence encoding a leader, modified such that it was optimized with an AT-rich sequence, resulted in a higher free energy for the predicted RNA structure and allowed efficient initiation by the cellular ribosomes. The stable RNA secondary structure is removed by increasing the free energy.

Therefore, according to the present invention, increasing the AU content in a coding sequence optimizes the sequence by reducing the corresponding RNA secondary structure's integrity, and resulting in increased protein expression/translation, by melting of the inhibitory secondary structures (stem loops) in the RNA transcript. The disruption of secondary structure integrity is particularly important in the 5' portion of the RNA or coding sequence, particularly the first 100 to 200 nucleotides of the RNA. In some embodiments, the AU or AT content is increased in the first 100 to 200 nucletides from the initiation of transcription, and in some embodiments the AU or AT content is increased in the first 100 to 200 nucleotides of the coding sequence or start of translation. In some embodiments, the disruption of secondary structure integrity of the RNA is achieved by full gene changes or alternating patterns within 100 to 200 nucleotide base stretches. Modification of the 3' end is also important.

The strategy of adding a leader-encoding sequence and altering the codons of that sequence to be yeast optimized (less frequently used codons in humans) is applicable to any gene encoding any protein, for example genes encoding viral proteins, including, but not limited to, the HIV-1 pol gene. AU-rich content is preferred; human dominant codons/ high GC content is not preferred. It has been discovered that lowering the stability of regions of secondary structure within mRNAs can be accomplished without prior knowledge of protein expression or structure. The resultant increased minimum free energy of the secondary structure that is predicted to form from the altered transcript renders the altered transcript capable of enhanced protein expression over the original.

Using standard techniques and readily available starting materials, a modified nucleic acid molecule may be prepared. The nucleic acid molecule may be incorporated into an expression vector which is then incorporated into a host cell. Host cells for use in well known recombinant expression systems for production of proteins are well known and readily available. Examples of host cells include bacteria cells such as *E. coli*, yeast cells such as *S. cerevisiae*, insect cells such as *S. frugiperda*, non-human mammalian tissue culture cells Chinese hamster ovary (CHO) cells and human tissue culture cells such as HeLa cells.

In some embodiments, for example, one having ordinary skill in the art can, using well known techniques, insert DNA molecules into a commercially available expression vector for use in well known expression systems. For example, the commercially available plasmid pSE420 (Invitrogen, San Diego, Calif.) may be used for production of immunomodulating proteins in *E. coli*. The commercially available plasmid pYES2 (Invitrogen, San Diego, Calif.) may, for example, be used for production in *S. cerevisiae* strains of yeast. The commercially available MAXBAC™ complete baculovirus expression system (Invitrogen, San Diego, Calif.) may, for example, be used for production in insect cells. The commercially available plasmid pcDNAI or pcDNA3 (Invitrogen, San Diego, Calif.) may, for example, be used for production in mammalian cells such as CHO cells. One having ordinary skill in the art can use these commercial expression vectors and systems or others to produce immunomodulating proteins by routine techniques and readily available starting materials. (See e.g., Sambrook et al., eds., 2001, supra) Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts (See e.g., Sambrook et al., eds., 2001, supra).

The expression vector including the modified DNA is used to transform the compatible host which is then cultured and maintained under conditions wherein expression of the foreign DNA takes place. The protein of the present invention thus produced is recovered from the culture, either by lysing the cells or from the culture medium as appropriate and known to those in the art. One having ordinary skill in the art can, using well known techniques, isolate the protein that is produced using such expression systems. The methods of purifying proteins from natural sources using antibodies may be equally applied to purifying protein produced by recombinant DNA methodology.

The pharmaceutical compositions of the present invention may be administered by any means that enables the active agent to reach the agent's site of action in the body of a mammal. The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, pulmonary administration, e.g., by inhalation or insufflation, or intrathecal or intraventricular administration.

The present invention further relates to injectable pharmaceutical compositions which comprise such nucleic acid molecules.

The injectable pharmaceutical compositions that comprise a modified nucleotide sequence operably linked to regulatory elements may be delivered using any of several well known technologies including DNA injection (also referred to as DNA vaccination), recombinant vectors such as recombinant adenovirus, recombinant adenovirus associated virus and recombinant vaccinia.

DNA vaccines are described in U.S. Pat. Nos. 5,593,972, 5,739,118, 5,817,637, 5,830,876, 5,962,428, 5,981,505, 5,580,859, 5,703,055, 5,676,594, and the priority applications cited therein, which are each incorporated herein by reference. In addition to the delivery protocols described in those applications, alternative methods of delivering DNA are described in U.S. Pat. Nos. 4,945,050 and 5,036,006, which are both incorporated herein by reference.

Routes of administration include, but are not limited to, intramuscular, intranasally, intraperitoneal, intradermal, subcutaneous, intravenous, intraarterially, intraoccularly and oral as well as topically, transdermally, by inhalation or suppository or to mucosal tissue such as by lavage to vaginal, rectal, urethral, buccal and sublingual tissue. Preferred routes of administration include to mucosal tissue, intramuscular, intraperitoneal, intradermal and subcutaneous injection. Genetic constructs may be administered by means including, but not limited to, traditional syringes, needleless injection devices, or "microprojectile bombardment gene guns".

When taken up by a cell, the genetic construct(s) may remain present in the cell as a functioning extrachromosomal molecule and/or integrate into the cell's chromosomal DNA. DNA may be introduced into cells where it remains as separate genetic material in the form of a plasmid or plasmids. Alternatively, linear DNA which can integrate into the chromosome may be introduced into the cell. When introducing DNA into the cell, reagents which promote DNA integration into chromosomes may be added. DNA sequences which are useful to promote integration may also be included in the DNA molecule. Alternatively, RNA may be administered to the cell. It is also contemplated to provide the genetic construct as a linear minichromosome including a centromere, telomeres and an origin of replication. Gene constructs may remain part of the genetic material in attenuated live microorganisms or recombinant microbial vectors which live in cells. Gene constructs may be part of genomes of recombinant viral vaccines where the genetic material either integrates into the chromosome of the cell or remains extrachromosomal.

Genetic constructs include regulatory elements necessary for gene expression of a nucleic acid molecule. The elements include: a promoter, an initiation codon, a stop codon, and a polyadenylation signal. In addition, enhancers are often required for gene expression of the sequence that encodes the target protein. It is necessary that these elements be operable linked to the sequence that encodes the desired proteins and that the regulatory elements are operably in the individual to whom they are administered. Initiation codons and stop codon are generally considered to be part of a nucleotide sequence that encodes the desired protein. However, it is necessary that these elements are functional in the individual to whom the gene construct is administered. The initiation and termination codons must be in frame with the coding sequence. Promoters and polyadenylation signals used must be functional within the cells of the individual. Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothionein. Examples of polyadenylation signals useful to practice the present invention, especially in the production of a genetic vaccine for humans, include but are not limited to SV40 polyadenylation signals and LTR polyadenylation signals. In particular, the SV40 polyadenylation signal which is inpCEP4 plasmid (Invitrogen, San Diego Calif.), referred to as the SV40 polyadenylation signal, is used. In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV. Genetic constructs can be provided with mammalian origin of replication in order to maintain the construct extrachromosomally and produce multiple copies of the construct in the cell. Plasmids pCEP4 and pREP4 from Invitrogen (San Diego, Calif.) contain the Epstein Barr virus origin of replication and nuclear antigen EBNA-1 coding region which produces high copy episomal replication without integration.

One method of the present invention comprises the steps of administering nucleic acid molecules intramuscularly, intranasally, intraperatoneally, subcutaneously, intradermally, or topically or by lavage to mucosal tissue selected from the group consisting of inhalation, vaginal, rectal, urethral, buccal and sublingual.

In some embodiments, the nucleic acid molecule is delivered to the cells in conjunction with administration of a polynucleotide function enhancer or a genetic vaccine facilitator agent. Polynucleotide function enhancers are described in U.S. Ser. No. 08/008,342 filed Jan. 26, 1993, U.S. Ser. No. 08/029,336 filed Mar. 11, 1993, U.S. Ser. No. 08/125,012 filed Sep. 21, 1993, and International Application Serial Number PCT/US94/00899 filed Jan. 26, 1994, which are each incorporated herein by reference. Genetic vaccine facilitator (GVF) agents are described in U.S. Ser. No. 08/221,579 filed Apr. 1, 1994, which is incorporated herein by reference. The co-agents which are administered in conjunction with nucleic acid molecules may be administered as a mixture with the nucleic acid molecule or administered separately simultaneously, before or after administration of nucleic acid molecules. In addition, other agents which may function as transfecting agents and/or replicating agents and/or inflammatory agents and which may be co-administered with a GVF include growth factors, cytokines and lymphokines such as a-interferon, gamma-interferon, platelet derived growth factor (PDGF), TNF, epidermal growth factor (EGF), IL-1, IL-2, IL-4, IL-6, IL-10 and IL-12 as well as fibroblast growth factor, surface active agents such as immune-stimulating complexes (ISCOMS), Freund's incomplete adjuvant, LPS analog including monophosphoryl Lipid A (MPL), muramyl peptides, quinone analogs and vesicles such as squalene and squalene, and hyaluronic acid may also be used administered in conjunction with the genetic construct. In some embodiments, an immunomodulating protein may be used as a GVF.

The pharmaceutical compositions according to the present invention comprise about 1 nanogram to about 2000 micrograms of DNA. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms of DNA. In some preferred embodiments, the pharmaceutical compositions contain about 100 to about 200 micrograms DNA.

The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

The present invention is useful to elicit broad immune responses against a target protein, i.e., proteins specifically associated with pathogens, allergens or the individual's own "abnormal" cells. The present invention is useful to immunize individuals against pathogenic agents and organisms such that an immune response against a pathogen protein provides protective immunity against the pathogen. The present invention is useful to combat hyperproliferative diseases and disorders such as cancer by eliciting an immune response against a target protein that is specifically associated with the hyperproliferative cells. The present invention is useful to combat autoimmune diseases and disorders by eliciting an immune response against a target protein that is specifically associated with cells involved in the autoimmune condition.

The nucleic acid molecule(s) may be provided as plasmid DNA, the nucleic acid molecules of recombinant vectors or as part of the genetic material provided in an attenuated vaccine or cell vaccine. Alternatively, in some embodiments, the target protein and/or wither or both immunomodulating proteins may be delivered as a protein in addition to the nucleic acid molecules that encode them or instead of the nucleic acid molecules that encode them.

The present invention may be used to immunize an individual against all pathogens such as viruses, prokaryotic and pathogenic eukaryotic organisms such as unicellular pathogenic organisms and multicellular parasites. The present invention is particularly useful to immunize an individual against those pathogens which infect cells and which are not encapsulated such as viruses, and prokaryotes such as gonorrhea, listeria and shigella. In addition, the present invention is also useful to immunize an individual against protozoan pathogens which include a stage in the life cycle where they are intracellular pathogens.

In order to produce a genetic vaccine to protect against pathogen infection, genetic material which encodes immunogenic proteins against which a protective immune response can be mounted must be included in a genetic construct as the coding sequence for the target. Whether the pathogen infects intracellularly, for which the present invention is particularly useful, or extracellularly, it is unlikely that all pathogen antigens will elicit a protective response. Because DNA and RNA are both relatively small and can be produced relatively easily, the present invention provides the additional advantage of allowing for vaccination with multiple pathogen antigens. The genetic construct used in the genetic vaccine can include genetic material which encodes many pathogen antigens. For example, several viral genes may be included in a single construct thereby providing multiple targets.

Another aspect of the present invention provides a method of conferring a broad based protective immune response against hyperproliferating cells that are characteristic in hyperproliferative diseases and to a method of treating individuals suffering from hyperproliferative diseases. Examples of hyperproliferative diseases include all forms of cancer and psoriasis.

It has been discovered that introduction of a genetic construct that includes a nucleotide sequence which encodes an immunogenic "hyperproliferating cell"-associated protein into the cells of an individual results in the production of those proteins in the vaccinated cells of an individual. To immunize against hyperproliferative diseases, a genetic construct that includes a nucleotide sequence which encodes a protein that is associated with a hyperproliferative disease is administered to an individual.

In order for the hyperproliferative-associated protein to be an effective immunogenic target, it must be a protein that is produced exclusively or at higher levels in hyperproliferative cells as compared to normal cells. Target antigens include such proteins, fragments thereof and peptides which comprise at least an epitope found on such proteins. In some cases, a hyperproliferative-associated protein is the product of a mutation of a gene that encodes a protein. The mutated gene encodes a protein which is nearly identical to the normal protein except it has a slightly different amino acid sequence which results in a different epitope not found on the normal protein. Such target proteins include those which are proteins encoded by oncogenes such as myb, myc, fyn, and the translocation gene bcr/abl, ras, src, P53, neu, trk and EGRF. In addition to oncogene products as target antigens, target proteins for anti-cancer treatments and protective regimens include variable regions of antibodies made by B cell lymphomas and variable regions of T cell receptors of T cell lymphomas which, in some embodiments, are also used target antigens for autoimmune disease. Other tumor-associated proteins can be used as target proteins such as proteins which are found at higher levels in tumor cells including the protein recognized by monoclonal antibody 17-1A and folate binding proteins.

While the present invention may be used to immunize an individual against one or more of several forms of cancer, the present invention is particularly useful to prophylactically immunize an individual who is predisposed to develop a particular cancer or who has had cancer and is therefore susceptible to a relapse. Developments in genetics and technology as well as epidemiology allow for the determination of probability and risk assessment for the development of cancer in individual. Using genetic screening and/or family health histories, it is possible to predict the probability a particular individual has for developing any one of several types of cancer.

Similarly, those individuals who have already developed cancer and who have been treated to remove the cancer or are otherwise in remission are particularly susceptible to relapse and reoccurrence. As part of a treatment regimen, such individuals can be immunized against the cancer that they have been diagnosed as having had in order to combat a recurrence. Thus, once it is known that an individual has had a type of cancer and is at risk of a relapse, they can be immunized in order to prepare their immune system to combat any future appearance of the cancer.

The present invention provides a method of treating individuals suffering from hyperproliferative diseases. In such methods, the introduction of genetic constructs serves as an immunotherapeutic, directing and promoting the immune system of the individual to combat hyperproliferative cells that produce the target protein.

The present invention provides a method of treating individuals suffering from autoimmune diseases and disorders by conferring a broad based protective immune response against targets that are associated with autoimmunity including cell receptors and cells which produce "self"-directed antibodies.

T cell mediated autoimmune diseases include rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease, and ulcerative colitis. Each of these diseases is characterized by T cell receptors that bind to endogenous antigens and initiate the inflammatory cascade associated with autoimmune diseases. Vaccination against the variable region of the T cells would elicit an immune response including CTLs to eliminate those T cells.

In RA, several specific variable regions of T cell receptors (TCRs) which are involved in the disease have been characterized. These TCRs include Vβ-3, Vβ-14, Vβ-17 and Vα-17. Thus, vaccination with a DNA construct that encodes at least one of these proteins will elicit an immune response that will target T cells involved in RA. See: Howell et al., 1991, Proc. Natl. Acad. Sci. USA, 88:10921–10925; Paliard et al., 1991, Science, 253:325–329; Williams et al., 1992, J. Clin. Invest., 90:326–333; each of which is incorporated herein by reference.

In MS, several specific variable regions of TCRs which are involved in the disease have been characterized. These TCRs include Vβ-7 and Vα-10. Thus, vaccination with a DNA construct that encodes at least one of these proteins will elicit an immune response that will target T cells involved in MS. See: Wucherpfennig et al., 1990, Science, 248:1016–1019; Oksenberg et al., 1990, Nature, 345:344–346; each of which is incorporated herein by reference.

In scleroderma, several specific variable regions of TCRs which are involved in the disease have been characterized. These TCRs include Vβ-6, Vβ-8, Vβ-14 and Vα-16, Vα-3C, Vα-7, Vα-14, Vα-15, Vα-16, Vα-28 and Vα-12. Thus, vaccination with a DNA construct that encodes at least one of these proteins will elicit an immune response that will target T cells involved in scleroderma.

In order to treat patients suffering from a T cell mediated autoimmune disease, particularly those for which the variable region of the TCR has yet to be characterized, a synovial biopsy can be performed. Samples of the T cells present can be taken and the variable region of those TCRs identified using standard techniques. Genetic vaccines can be prepared using this information.

B cell mediated autoimmune diseases include systemic lupus erythematosus (SLE), Grave's disease, myasthenia gravis, autoimmune hemolytic anemia, autoimmune thrombocytopenia, asthma, cryoglobulinemia, primary biliary sclerosis, and pernicious anemia. Each of these diseases is characterized by antibodies which bind to endogenous antigens and initiate the inflammatory cascade associated with autoimmune diseases. Vaccination against the variable region of antibodies would elicit an immune response including CTLs to eliminate those B cells that produce the antibody.

In order to treat patients suffering from a B cell mediated autoimmune disease, the variable region of the antibodies involved in the autoimmune activity must be identified. A biopsy can be performed and samples of the antibodies present at a site of inflammation can be taken. The variable region of those antibodies can be identified using standard techniques. Genetic vaccines can be prepared using this information.

In the case of SLE, one antigen is believed to be DNA. Thus, in patients to be immunized against SLE, their sera can be screened for anti-DNA antibodies and a vaccine can be prepared which includes DNA constructs that encode the variable region of such anti-DNA antibodies found in the sera.

Common structural features among the variable regions of both TCRs and antibodies are well known. The DNA sequence encoding a particular TCR or antibody can generally be found following well known methods such as those described in Kabat et al., 1987, *Sequence of Proteins of Immunological Interest*, U.S. Department of Health and Human Services, Bethesda Md., which is incorporated herein by reference. In addition, a general method for cloning functional variable regions from antibodies can be found in Chaudhary et al., 1990, Proc. Natl. Acad. Sci. USA, 87:1066, which is incorporated herein by reference.

In some of the embodiments of the invention that relate to gene therapy, the gene constructs contain either compensating genes or genes that encode therapeutic proteins. Examples of compensating genes include a gene which encodes dystrophin or a functional fragment, a gene to compensate for the defective gene in patients suffering from cystic fibrosis, an insulin, a gene to compensate for the defective gene in patients suffering from ADA, and a gene encoding Factor VIII. Examples of genes encoding therapeutic proteins include genes which encodes erythropoietin, interferon, LDL receptor, GM-CSF, IL-2, IL-4 and TNF. Additionally, genetic constructs which encode single chain antibody components which specifically bind to toxic substances can be administered. In some preferred embodiments, the dystrophin gene is provided as part of a mini-gene and used to treat individuals suffering from muscular dystrophy. In some preferred embodiments, a mini-gene which contains coding sequence for a partial dystrophin protein is provided. Dystrophin abnormalities are responsible for both the milder Becker's Muscular Dystrophy (BMD) and the severe Duchenne's Muscular Dystrophy (DMD). In BMD dystrophin is made, but it is abnormal in either size and/or amount. The patient is mild to moderately weak. In DMD no protein is made and the patient is chairbound by age 13 and usually dies by age 20. In some patients, particularly those suffering from BMD, partial dystrophin protein produced by expression of a mini-gene delivered according to the present invention can provide improved muscle function.

In some preferred embodiments, genes encoding IL-2, IL-4, interferon, or TNF are delivered to tumor cells which are either present or removed and then reintroduced into an individual. In some embodiments, a gene encoding gamma interferon is administered to an individual suffering from multiple sclerosis.

In addition to using modified nucleic acid sequences to improve genetic vaccines, the present invention relates to improved attenuated live vaccines and improved vaccines which use recombinant vectors to deliver foreign genes that encode antigens. Examples of attenuated live vaccines and those using recombinant vectors to deliver foreign antigens are described in U.S. Pat. Nos. 4,722,848; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; and 5,482,713, which are each incorporated herein by reference. Gene constructs are provided which include the modified nucleotide sequence operably linked to regulatory sequences that can function in the vaccinee to effect expression. The gene constructs are incorporated in the attenuated live vaccines and recombinant vaccines to produce improved vaccines according to the invention. Likewise modified nucleic acid sequences can be used in recombinant vectors useful to deliver gene therapeutics that encode desired proteins.

The present invention provides an improved method of immunizing individuals that comprises the step of delivering gene constructs to the cells of individuals as part of vaccine compositions which include are provided which include DNA vaccines, attenuated live vaccines and recombinant vaccines. The gene constructs comprise a nucleotide sequence that encodes an immunomodulating protein and that is operably linked to regulatory sequences that can function in the vaccinee to effect expression. The improved vaccines result in an enhanced cellular immune response.

The invention is further illustrated by way of the following examples, which are intended to elaborate several embodiments of the invention. These examples are not intended, nor are they to be construed, as limiting the scope of the invention. It will be clear that the invention may be practiced otherwise than as particularly described herein. Numerous modifications and variations of the present invention are possible in view of the teachings herein and, therefore, are within the scope of the invention.

EXAMPLES

Example 1

Materials and Methods
Prediction of mRNA secondary structure

To enhance translation efficiency of transgenes, RNA secondary structure was predicted by using MulFold and viewed by LoopDloop software for the Macintosh computer.
Immunoprecipitation of radiolabeled in vitro translated proteins $^{35}$S-labeled protein products were prepared using the TNT-T7 coupled Transcription/Translation System (Promega). 10 ml of radiolabeled protein sample and 1 ml of anti-His (C-term) antibody (Invitrogen, CA) were added to 300 $\mu$l of RIPA buffer and mixed gently. After an incubation at 4° C. for 90 minutes, Protein A-Sepharose beads (Amersham-Pharmacia Biotech, Piscataway, N.J.) was added to the protein-antibody complexes at a final concentration of 5 mg per tube and the samples were then incubated at 4° C. for 90 minutes in a rotating shaker. The beads were washed three times with RIPA buffer and suspended in 2x SDS sample buffer. The immunoprecipitated protein complexes were eluted from the Sepharose beads by brief boiling and resolved in SDS/PAGE (15%) gels. The mobility of the protein samples was compared with that of commercially available $^{14}$C-methylated molecular weight marker (Sigma-Aldrich Corp., St. Louis, Mo.). The gel was fixed, treated briefly with 1M sodium salicylate solution and dried in a gel drier (BioRad, Hercules, Calif.). The dried gel was exposed overnight to X-ray film (Kodak, Rochester, N.Y.). The molecular size of the in vitro translated protein was 21.5 kD.

In vitro translated protein

Non-radioactive, in vitro translated Cp protein was also generated as described above, using the TNT-T7 coupled Transcription/Translation System (Promega, Madison, Wis.) with non-radioactive components. An in vitro translation control was generated using the in vitro translation kit with the pcDNA3.1 vector (Invitrogen, San Diego, Calif.), lacking an expressible insert.

DNA inoculation of mice

The quadriceps muscles of 6- to 8-week-old female BALB/c mice (Harlan Sprague Dawley, Inc., Indianapolis, Ind.) were injected with 100 $\mu$g of pWNVh-DJY, pWNVy-DJY, or pcDNA3.1 in phosphate buffered saline (PBS) and 0.25% bupivacaine-HCl (Sigma, St. Louis, Mo.). Mice were injected with two DNA immunizations (100 $\mu$g each) separated by two weeks. At thirteen days after the boost injection, the mice were sacrificed, the spleens were harvested, and the lymphocytes were isolated and tested for cellular immune responses.

Intracellular IFN-γ detection by flow cytometry

In each well of a round-bottom 96-well plate was placed 100 μl of RPMI-1640 (supplemented with 5% FBS), containing 50 U/ml rHuIL-2 (Intergen, Purchase, N.Y.), 10 μg/ml Brefeldin A (Pharmingen, San Diego, Calif.), 100 ng/ml PMA (Sigma, St. Louis, Mo.), and 1 μg/ml ionomycin (Sigma, St. Louis, Mo.). Either in vitro translated protein or an in vitro translation control (generated using the in vitro translation kit with the vector backbone lacking an expressible insert), at 4 μg/ml was added in 50 μl of R5 medium. After adding the antigens (Ags), isolated splenocytes were added to each well at 1×10⁶ cells in 50 μl of R5 medium. For the compensation in flow cytometry, splenocytes from naïve mice were set up with only IL-2 and Brefeldin A. The plates were incubated in 37° C., 5% $CO_2$ in an incubator for 5 to 6 hours. As a control, cells were incubated without Ag. After incubation, the plate was spun at 1200 rpm for 5 minutes and the supernatants discarded. The cells were resuspended with 200 μl of PBS, supplemented with 1% BSA, and put on ice for 15 minutes, and then spun down and resuspended with anti-CD4-PE mAb (Pharmingen) at 0.1 μg/sample in 50 μl of PBS/1% BSA. After incubation for 30 minutes at 4° C., the cells were washed twice with PBS/1%. After the second wash, cell pellets were resuspended with 100 μl of Cytofix/Cytoperm solution (Pharmingen) and incubated for 20 minutes at 4° C. The cells were washed twice with 1× Perm/Wash (Pharmingen) and resuspended with 50 μl of Penn/Wash solution containing anti-IFN-γ-APC 916(Pharmingen) at 0.1 μg/sample concentration. After incubation for 30 minutes at 4° C., the cells were washed twice with 1× Perm/Wash solution and fixed with 2% paraformaldehyde, and then stored at 4° C. until analyzed by flow cytometry.

Example 2

Addition of Leader Sequence to West Nile Virus Capsid mRNA.

The addition of a leader sequence to minimize free energy in the West Nile Virus Capsid mRNA resulted in enhanced protein expression and immune response.

To enhance the transcription and translation efficiency of transgenes, the human IgE leader sequence was added to the 5' upstream of open reading frame (orf) sequences (FIG. 1).

The addition of a sequence encoding the human IgE leader sequence containing codons that are less prevalently utilized in humans (WNVy-DJY construct (yeast codon)) resulted in a predicted secondary structure for the mRNA having an increased free energy value, relative to the secondary structure for the mRNA without the leader sequence (WNVwt construct (wild type)), or relative to the secondary structure for the mRNA encoding a leader sequence optimized with human codons (WNVh-DJY construct (human codon)) (FIG. 2).

Furthermore, the construct encoding the leader sequence containing codons that are less prevalently utilized in humans (yeast optimized) yielded a higher level of protein than did the construct encoding the leader sequence containing human optimized codons, as determined by immunoprecipitation of radiolabeled in vitro translated proteins (FIG. 3; Table 1, yeast codon usage). The codons more prevalently used by yeast are, in general, AU rich; the codons more prevalently used by Homo sapiens are, in general, more GC rich (see Kim et al., 1997, Gene, supra).

TABLE 1

Yeast codon prevalent usage.

| Amino Acid | | Yeast codon |
|---|---|---|
| A | Ala | GCU |
| R | Arg | AGA |
| N | Asn | AAU |
| D | Asp | GAU |
| C | Cys | UGU |
| Q | Gln | CAA |
| E | Glu | GAA |
| G | Gly | GGU |
| H | His | CAU |
| I | Ile | AUU |
| L | Leu | UUA |
| K | Lys | AAA |
| P | Pro | CCA |
| F | Phe | UUU |
| S | Ser | UCU |
| T | Thr | ACU |
| W | Trp | UGG |
| Y | Tyr | UAU |
| V | Val | GUU |

Figure 4:
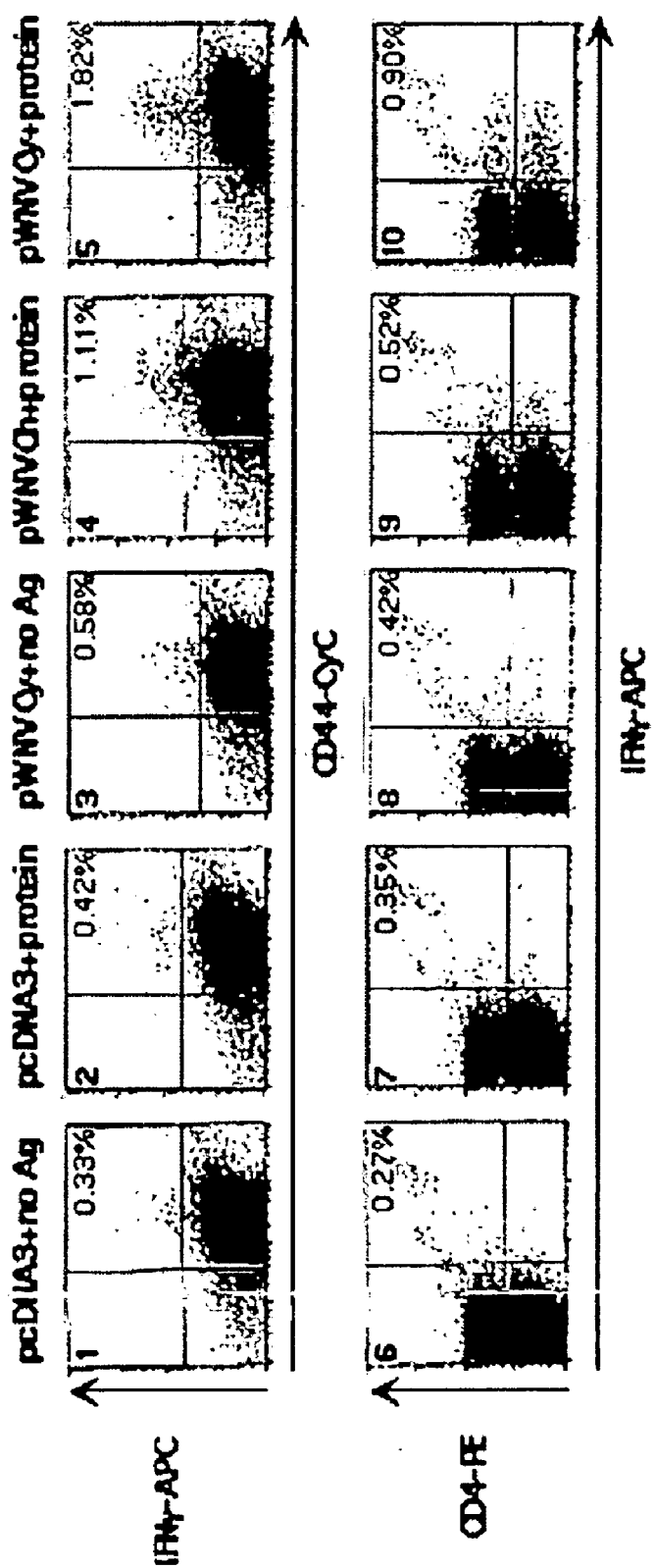
FIG. 4 presents the flow cytometry analysis of intracellular IFN-γ expression in in vitro stimulated splenocytes from DNA immunized mice. Values presented are the percentage dual positive cells. In the upper panels, the cells were stained for INF-γ and CD44; in the lower panels the cells were stained for CD4 and INF-γ. The labeling across the top indicates the vector used to immunize the mice plus the stimulus used for the in vitro restimulation of the splenocytes. The immunizing vectors were pcDNA3 (pcDNA3.1), pWNVh-DJY (pWNVCh), and pWNVy-DJY (pWNVCy). "No Ag" indicates that the splenocytes were incubated with an in vitro translation control (described in Example 2), "protein" indicates that the splenocytes were incubated with in vitro translated Cp protein product from the pWNVy-DJY expression construct.

DNA plasmid injection into mouse muscle induced an antigen-specific, CD4⁺ Th cell-dependent immune response, as determined by intracellular IFN-γ/flow cytometry analysis. The CD4⁺ Th cell-dependent, intracellular INF-γ production was quantitated by flow cytometry. Splenocytes isolated from pWNVy-DJY (pWNVCy)-immunized mice, expressed higher levels IFN-γ, upon stimulation with in vitro translated Cp protein, than did the splenocytes isolated from pWNVh-DJY (pWNVCh)-immunized mice (see FIG. 4)

Example 3

Removal of RNA Secondary Structure in HIV-1 pol RNA by Increasing the Minimum Predicted Free Energy.

Figure 5:
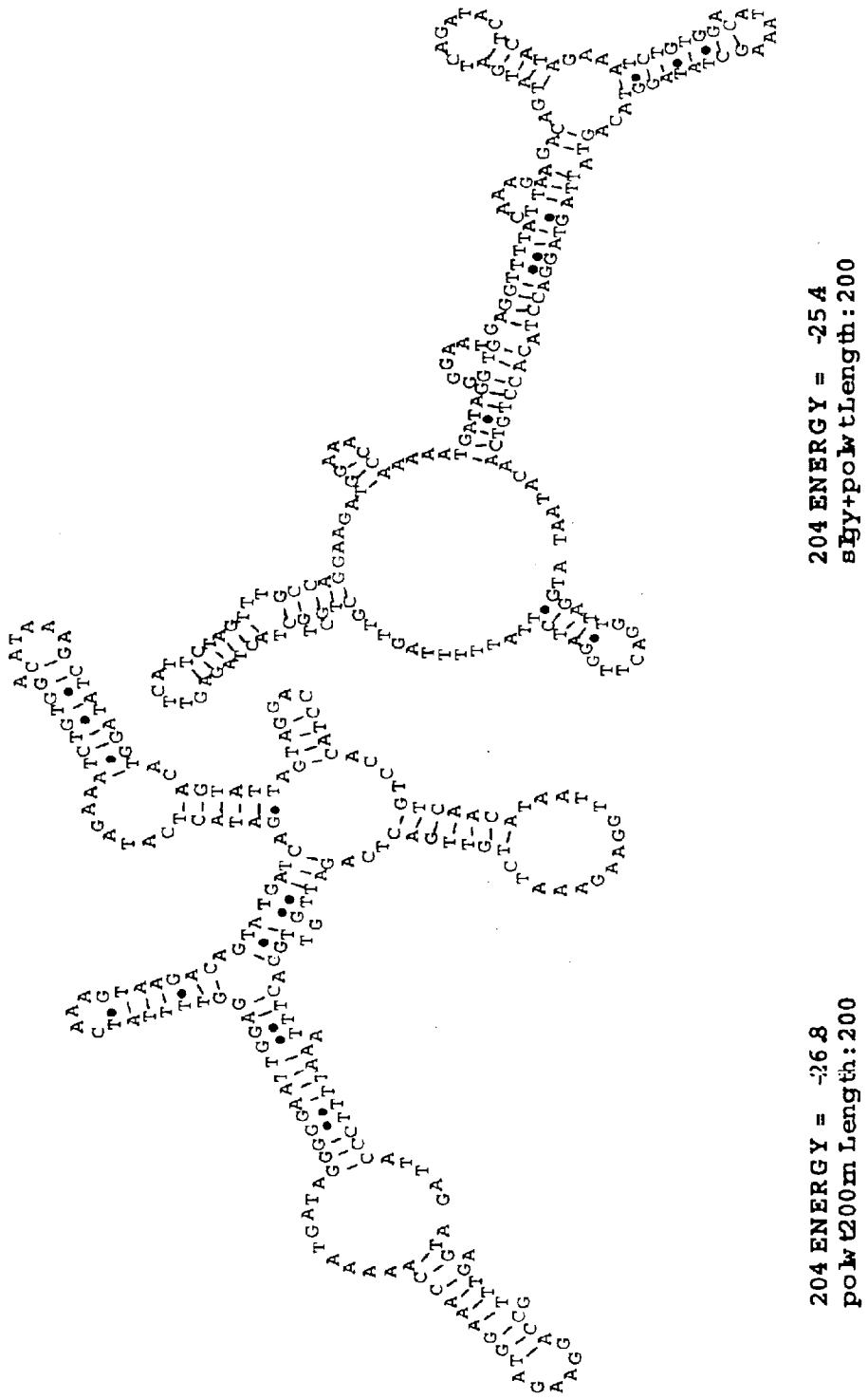
FIG. 5 presents the MulFold predicted RNA secondary structure with free energy values based upon energy minimization for the first 200 nucleotides of the wild type mRNA for to the HIV-1 pol gene (polwt200m) and for the fist 200 nucleotides of an mRNA for HIV-1 pol gene including a 5' sequence encoding the IgE leader sequence with codons less prevalently used in humans (yeast optimized) (sIgy+polwt). As shown, "T" represents "U" in the RNA strand.

The strategy of adding a leader encoding sequence and altering the codons to be yeast optimized (less frequently used in human) was applied to the HIV-1 pol gene. When nucleic acid sequence encoding the IgE leader sequence with codons less prevalently used in humans (yeast optimized) was added to the 5' end of HIV-1 pol gene, the predicted free energy of the energy minimized transcript was increased (FIG. 5).

Figure 6:
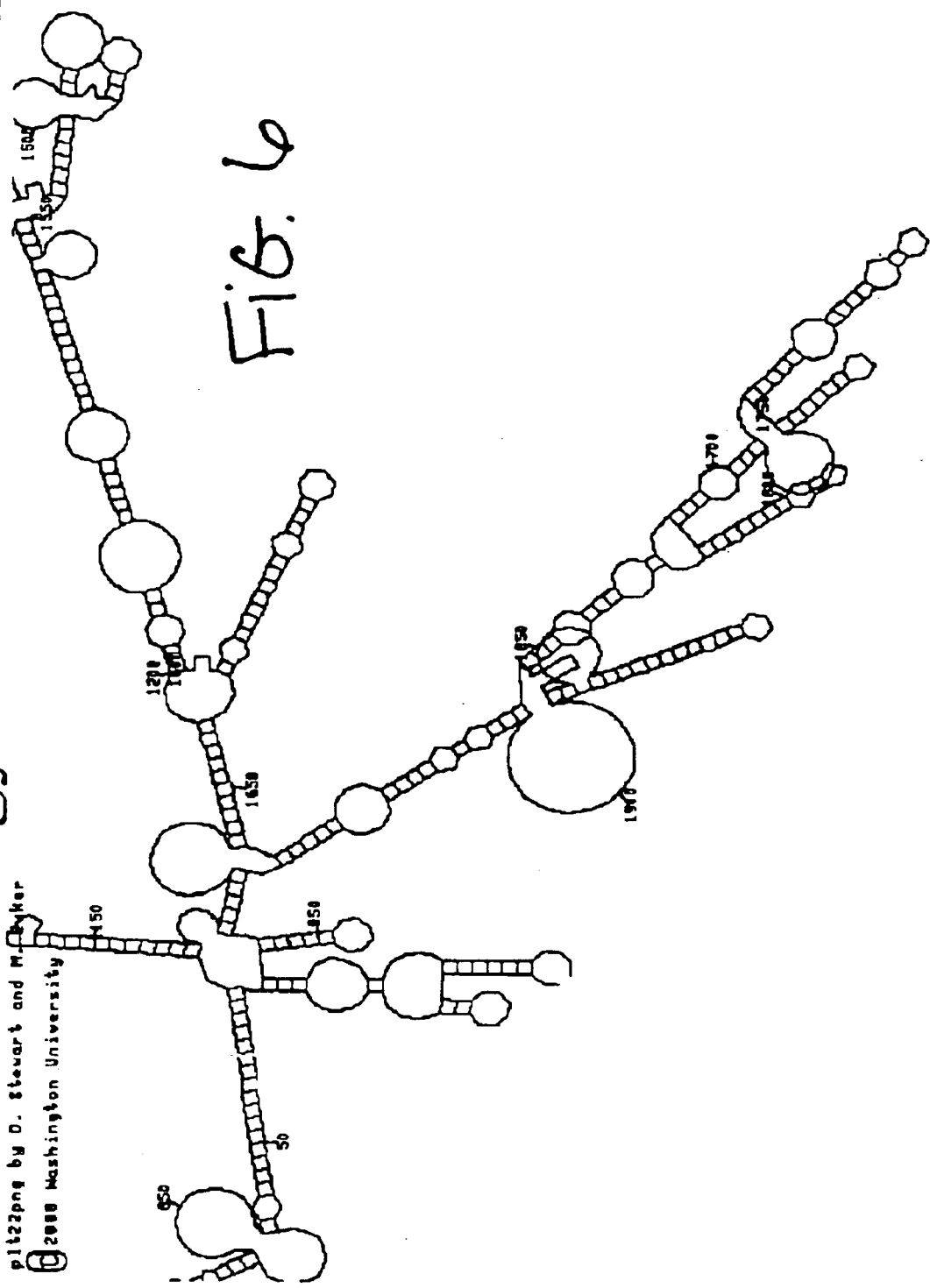
FIG. 6 presents the MulFold predicted secondary structure of the mRNA for the HIV-1 pol structural gene.
Figure 7:
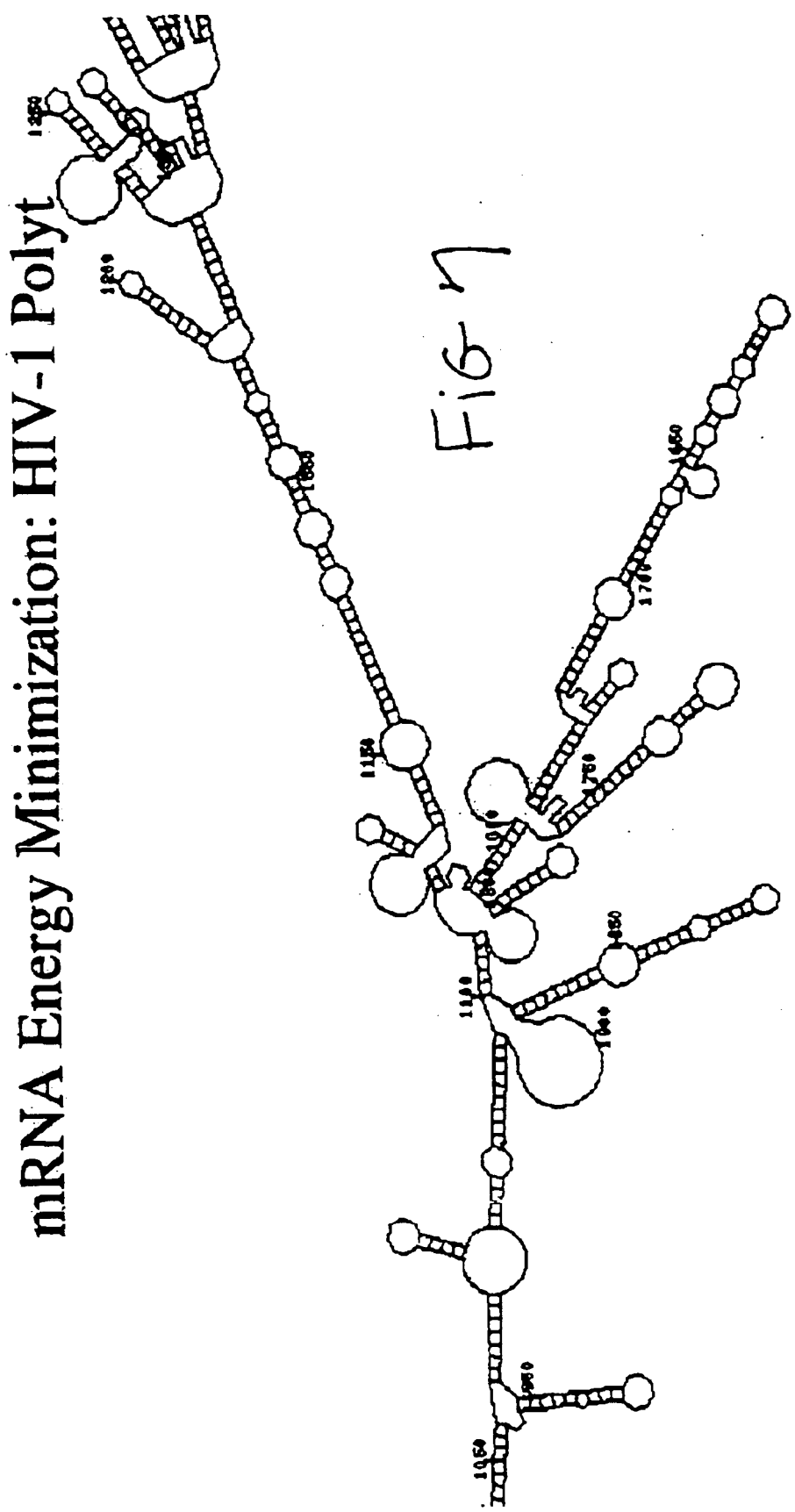
FIG. 7 presents the MulFold predicted secondary structure for the mRNA for the HIV-1 pol structural gene after the 200 nucleotide region of the sequence from nucleotide 1738 through nucleotide 1938 has been altered to contain codons that are less prevalently utilized in humans (yeast optimized codons).
Figure 8:
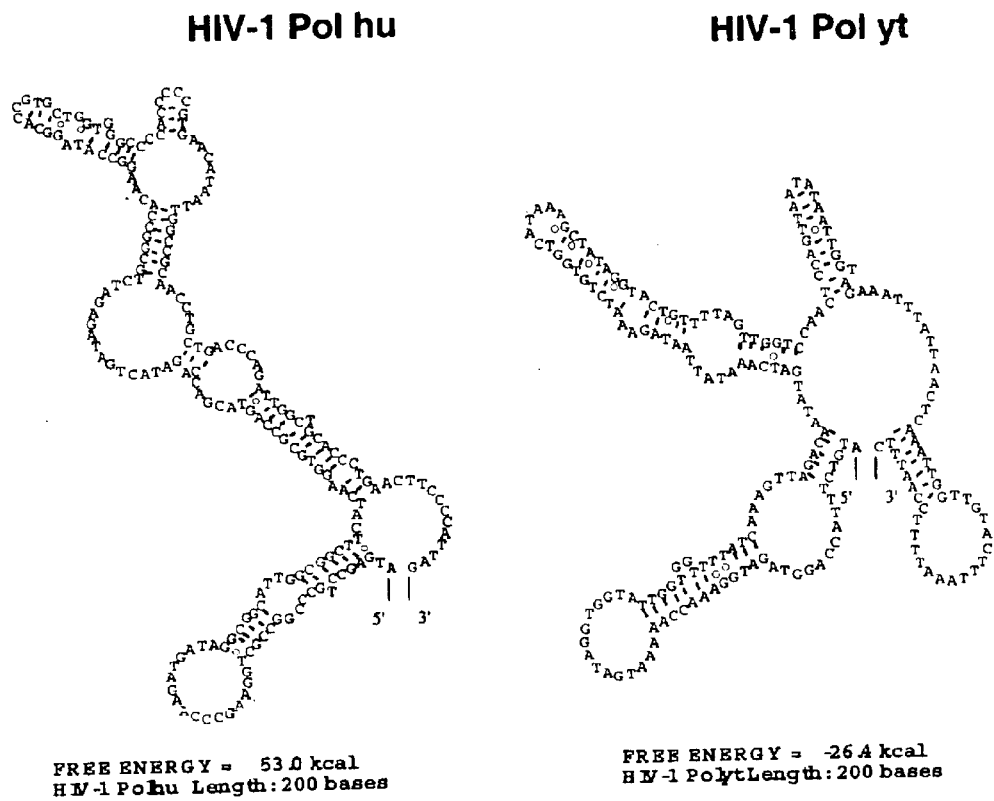
FIG. 8 presents the MulFold predicted secondary structure and overall free energy value for the first 200 nucleotides of the mRNA for the HIV-1 pol gene containing human optimized codons (HIV-1 Pol hu), and for the mRNA for the HIV-1 pol gene containing codons less prevalently utilized in humans (yeast optimized codons) (HIV-1 Pol yt). As shown, "T" represents "U" in the RNA strands.

In HIV-1 pol structural gene, several regions of stable secondary structure, located between nucleotide (nt) 1738 and nt 1938, were predicted by MulFold analysis (FIG. 6). Alteration of the codons in the region from nt 1738 to nt 1938 to codons less prevalently utilized in humans (yeast optimized codons) resulted in a weakening of the secondary structure in that region. The predicted secondary structure for the region with the modified codons had a higher free energy than the predicted secondary structure for the original sequence (FIG. 7). In addition, the formation of mRNA secondary structure in the first 200 nucleotides of the pol gene was minimized by using codons less prevalently utilized in humans (yeast optimized codons) (HIV-1 Pol yt), as compared to a transcript containing the most prevalently utilized codons in humans (human optimized codons) (HIV-1 Pol hu) (FIG. 8). The minimum free energy was dramatically increased from −53.0 kcal to −26.4 kcal.

Example 4

Removal of RNA Secondary Structure in HIV-1 gag RNA by Increasing the Minimum Predicted Free Energy.

Figure 9:
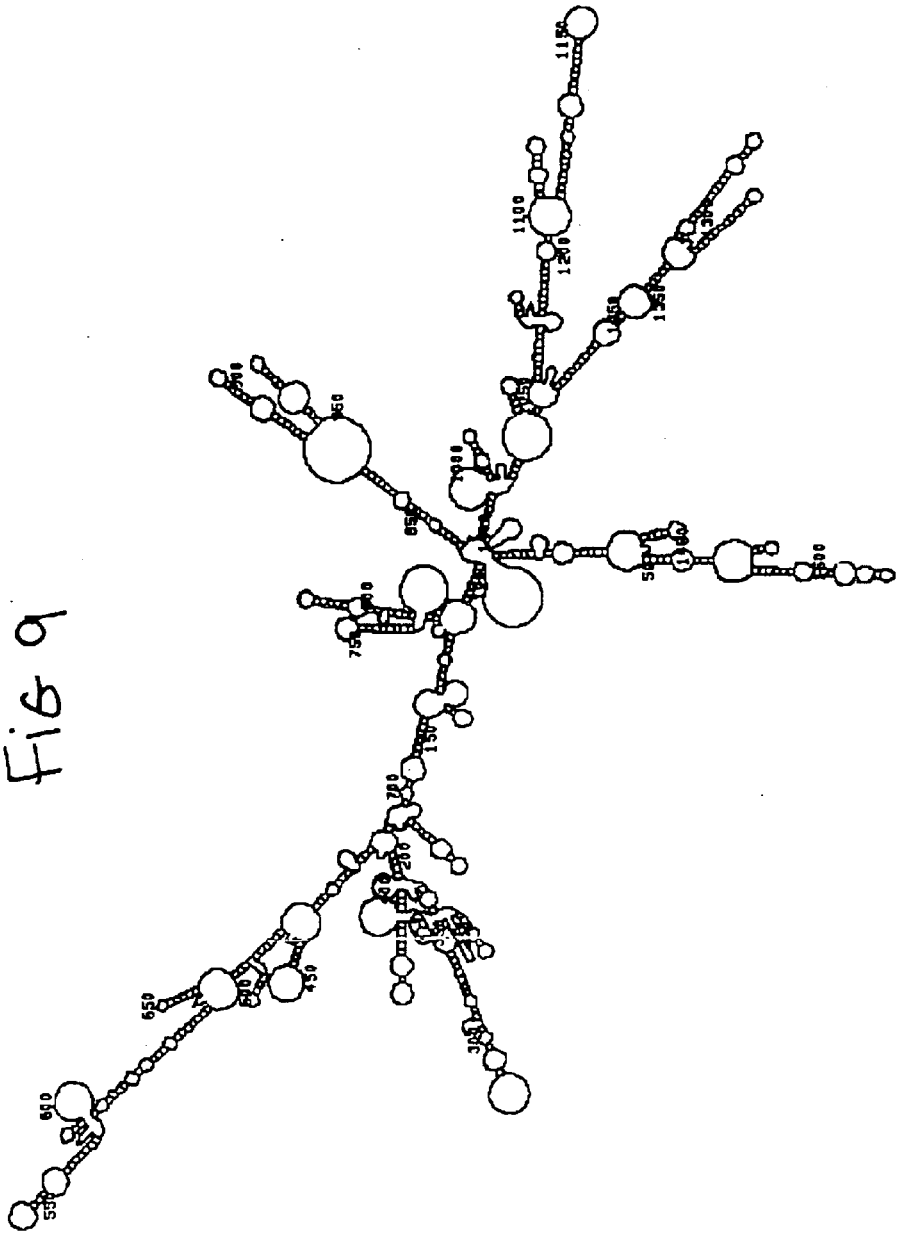
FIG. 9 presents the MulFold predicted secondary structure and overall free energy value for the mRNA transcript for the HIV-1 gag structural gene.
Figure 10:
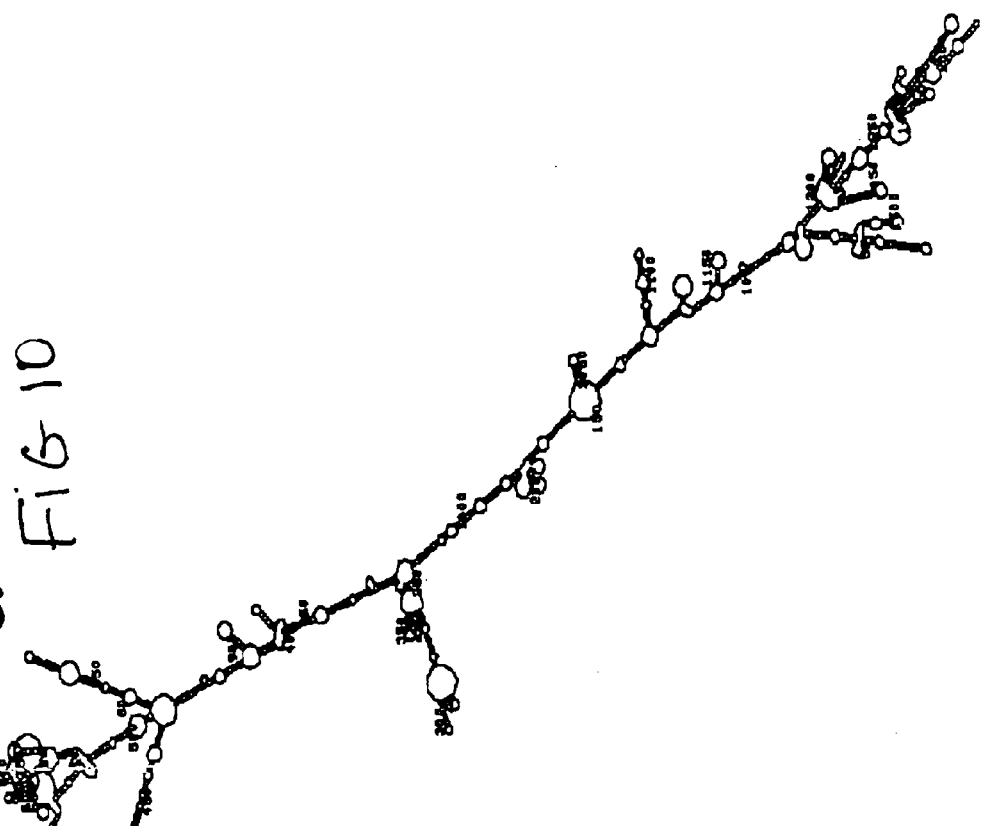
FIG. 10 presents the MulFold predicted secondary structure and overall free energy value for the mRNA transcript for the HIV-1 gag structural gene altered with codons that are utilized less prevalently in humans (yeast optimized).

Several regions of regions of stable secondary structure were predicted by MulFold analysis for the transcript for the HIV-1 gag structural gene (FIG. 9), and the minimum free energy was increased (from −351.07 kcal to −283.11 kcal) by using codons that are utilized less prevalently in humans (yeast optimized) (FIG. 10).

Example 5

Removal of RNA Secondary Structure in WNV env RNA by Increasing the Minimum Predicted Free Energy.

In the West Nile Virus envelope (env) gene, application of the strategy of mRNA energy minimization in the first 200 base pairs (bp) of the gene with codons that are utilized less prevalently in humans (yeast optimized, WNVyt200) increased the minimum free energy of the cognate transcript as compared to the transcript for the wild type WNV env gene (WNVwt200) or as compared to a transcript optimized with the most prevalently used codons in humans (WNVhu200) (FIG. 11).

The foregoing examples are meant to illustrate the invention and are not to be construed to limit the invention in any way. Those skilled in the art will recognize modifications that are within the spirit and scope of the invention.

All references cited herein are hereby incorporated by reference in their entirety.

What is claimed is:

1. A method of producing a protein in a recombinant expression system that comprises translation of mRNA transcribed from a heterologous DNA sequence in the expression system, said method comprising the steps of:
   a) predicting the secondary structure of mRNA transcribed from a native heterologous DNA sequence;
   b) modifying the native heterologous DNA sequence to produce a modified heterologous DNA sequence wherein mRNA transcribed from the modified heterologous DNA sequence has a secondary structure having increased free energy compared to that of the secondary structure of the mRNA transcribed from the native heterologous DNA sequence, wherein said modified heterologous DNA sequence comprises an IgE signal leader sequence; and
   c) using the modified heterologous DNA sequence in the recombinant expression system for protein production.

2. The method of claim 1 wherein said IgE leader sequence comprises SBQ ID NO: 1.

3. The method of claim 1 wherein said recombinant expression system is selected from the group consisting of: a cell free in vitro transcription and translation system; an in vitro cell expression system; a DNA construct used in direct DNA injection; and a recombinant vector for delivery to an individual.

4. A method of producing a protein in a recombinant expression system that comprising the steps of:
   a) modifying a native heterologous DNA sequence, wherein said modification comprises an IgE leader sequence; and
   b) using the modified heterologous DNA sequence in the recombinant expression system for protein production.

5. The method of claim 4 wherein said IgE leader sequence comprises SEQ ID NO: 1.

6. The method of claim 4 wherein said recombinant expression system is selected from the group consisting of: a cell free in vitro transcription and translation system; an in vitro cell expression system; a DNA construct used in direct DNA injection; and a recombinant vector for delivery to an individual.

7. An isolated DNA molecule for producing a protein in a recombinant expression system that comprises translation of mRNA transcribed from a heterologous DNA sequence in the expression system, wherein said DNA molecule comprises a modified heterologous DNA sequence comprising a nucleotide sequence encoding an IgE leader sequence wherein said modified heterologous DNA sequence has a secondary structure having increased free energy compared to that of the secondary structure of the mRNA transcribed from the native heterologous DNA sequence.

8. The isolated DNA molecule of claim 7 wherein said IgE leader sequence comprises SEQ ID NO: 1.

9. A recombinant viral vector comprising a nucleic acid molecule that includes a modified coding sequence encoding a protein operably linked to regulatory elements, wherein said modified coding sequence comprises an IgE lender sequence.

10. The recombinant viral, vector of claim 9 wherein said modified coding sequence comprises SEQ ID NO: 1.

* * * * *

UNITED STATES PATENT AND TRADEMARK OFFICE
CERTIFICATE OF CORRECTION

PATENT NO.        : 6,733,994 B2                                              Page 1 of 1
APPLICATION NO. : 09/971806
DATED             : May 11, 2004
INVENTOR(S)       : David B. Weiner and Joo-Sung Yang It is certified that error appears in the above-identified patent and that said Letters Patent is hereby corrected as shown below:

At Column 23, line 44, "SBQ" should read --SEQ--.

At Column 24, line 52, "The recombinant viral," should read --The recombinant viral--.

Signed and Sealed this

Seventh Day of August, 2007

JON W. DUDAS
*Director of the United States Patent and Trademark Office*

```
SEQUENCE LISTING

<160> NUMBER OF SEQ ID NOS: 4

<210> SEQ ID NO 1
<211> LENGTH: 54
<212> TYPE: DNA
<213> ORGANISM: Homo sapiens

<400> SEQUENCE: 1
atggactgga cctggatcct cttcttggtg gcagcagcca cgcgagtcca ctcc          54

<210> SEQ ID NO 2
<211> LENGTH: 18
<212> TYPE: PRT
<213> ORGANISM: Homo sapiens

<400> SEQUENCE: 2

Met Asp Trp Thr Trp Ile Leu Phe Leu Val Ala Ala Thr Arg Val
1               5                   10                  15

His Ser

<210> SEQ ID NO 3
<211> LENGTH: 122
<212> TYPE: PRT
<213> ORGANISM: West Nile virus

<400> SEQUENCE: 3

Ser Lys Lys Pro Gly Gly Pro Gly Lys Ser Arg Ala Val Asn Met Leu
1               5                   10                  15

Lys Arg Gly Met Pro Arg Val Leu Ser Leu Ile Gly Leu Lys Arg Ala
            20                  25                  30

Met Leu Ser Leu Ile Asp Gly Lys Gly Pro Ile Arg Phe Val Leu Ala
        35                  40                  45

Leu Leu Ala Phe Phe Arg Phe Thr Ala Ile Ala Pro Thr Arg Ala Val
    50                  55                  60

Leu Asp Arg Trp Arg Gly Val Asn Lys Gln Thr Ala Met Lys His Leu
65                  70                  75                  80

Leu Ser Phe Lys Lys Glu Leu Gly Thr Leu Thr Ser Ala Ile Asn Arg
                85                  90                  95

Arg Ser Ser Lys Gln Lys Lys Arg Gly Gly Lys Thr Gly Ile Ala Val
            100                 105                 110

Met Ile Gly Leu Ile Ala Ser Val Gly Ala
            115                 120

<210> SEQ ID NO 4
```

-continued

```
<211> LENGTH: 451
<212> TYPE: DNA
<213> ORGANISM: Artificial Sequence
<220> FEATURE:
<223> OTHER INFORMATION: Plasmid

<400> SEQUENCE: 4
cccaagcttg ccgccaccat ggactggacc tggatcctgt tcctggtggc cgccgccacc      60
cgcgtgcaca gctctaagaa accaggaggc cccggcaaga gccgcgccgt gaacatgctg     120
aagcgcggca tgccccgcgt gctgagcctg attggcctga agcgcgccat gctgagcctg     180
atcgacggca agggccccat acgcttcgtg ctggccctgc tggccttctt ccgcttcacc     240
gccattgccc ccacccgcgc cgtgctggac cgctggcgcg gcgtgaacaa gcagaccgcc     300
atgaagcacc tgctgagctt caagaaggag ctgggcaccc tgaccagcgc catcaaccgc     360
cgcagcagca agcagaagaa gcgcggcggc aagaccggca ttgccgtgat gattggcctg     420
atcgccagcg tgggcgcggc cgctaaacta t                                    451
```